United States Patent [19]
Bock et al.

[11] Patent Number: 4,926,456
[45] Date of Patent: May 15, 1990

[54] X-RAY EXAMINATION TABLE

[75] Inventors: Hans-Christian Bock; Karlheinz Kaul, both of Uttenreuth; Willi Schaefer, Erlangen, all of Fed. Rep. of Germany

[73] Assignee: Siemens Aktiengesellschaft, Berlin and Munich, Fed. Rep. of Germany

[21] Appl. No.: 277,407

[22] Filed: Nov. 28, 1988

Related U.S. Application Data

[63] Continuation of Ser. No. 029,790, Mar. 25, 1987, abandoned.

[30] Foreign Application Priority Data

May 7, 1986 [DE] Fed. Rep. of Germany ... 8612495[U]

[51] Int. Cl.$^5$ .............................................. G03B 42/02
[52] U.S. Cl. ..................................... 378/177; 378/196; 378/209
[58] Field of Search ......... 378/177.195, 208, 178–180, 378/196, 209

[56] References Cited

U.S. PATENT DOCUMENTS 3,843,112 10/1974 McDonald ........................... 378/209
4,298,801 11/1981 Heitman et al. ..................... 378/177
4,674,107 6/1987 Urban et al. ......................... 378/209

FOREIGN PATENT DOCUMENTS 2260140 6/1974 Fed. Rep. of Germany .
2308214 8/1974 Fed. Rep. of Germany ...... 128/376
3226374 1/1984 Fed. Rep. of Germany .
1400356 4/1965 France .
2255038 7/1975 France .
0047958 3/1982 United Kingdom ................ 378/209

OTHER PUBLICATIONS

Siemens sale brochure "MULTIGRAPH", A910-01-M1026-G232-01, 1985.

Primary Examiner—Craig E. Church
Attorney, Agent, or Firm—Hill, Van Santen, Steadman & Simpson

[57] ABSTRACT

An x-ray examination table comprises a table mounted on a pedestal which has a control box containing control elements for the device. The control box is displaceable in a longitudinal direction to the table so that a physician can easily reach the control elements in the control box given examination in the head area of the patient which is opposite to the position of the pedestal.

1 Claim, 1 Drawing Sheet

X-RAY EXAMINATION TABLE

This is a continuation of application Ser. No. 029,790, filed Mar. 25, 1987, now abandoned.

BACKGROUND OF THE INVENTION

The present invention is directed to an x-ray examination table comprising a pedestal on which a control box having control elements is arranged.

It is known to undertake the control of an x-ray examination apparatus having an x-ray examination table in such fashion that the control elements are in a control box of the examination table and are used for actuating the apparatus. For some examinations, for example at the head or foot of the patient, the physician must move relatively far from the control box. Accordingly, operations are rendered more difficult for such examinations because the control box is arranged at one end of the examination table so that it does not disturb or interfere with the introduction of the x-ray film cassette under the examination table.

SUMMARY OF THE INVENTION

The object of the present invention is to provide an x-ray examination table having a control box for the x-ray examination apparatus which has control elements that can be easily reached in all examinations which will occur.

To accomplish these goals, the present invention is an improvement in an x-ray examination table having a pedestal on which a control box comprising control elements is arranged, the improvements are that the control box is mounted on the pedestal by means for displacing the control box in a longitudinal direction of the table.

Given the x-ray examination table of the invention, the control box, which is arranged at one end of the examination table, can be displaced in the direction towards the working position of the physician when the physician works at the other end so that his control element can always be easily reached.

Other advantages of the invention will be readily apparent from the following description, drawings and the claims.

DESCRIPTION OF THE PREFERRED EMBODIMENTS

Figure 1:
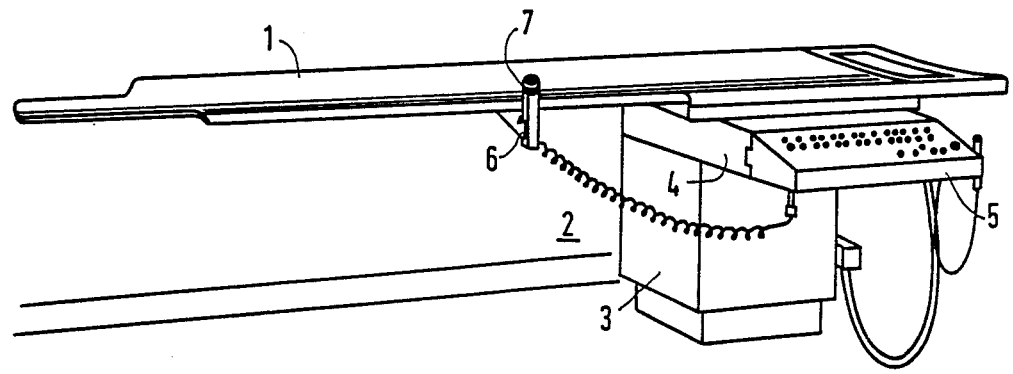
FIG. 1 is a perspective view of an x-ray examination table in accordance with the present invention with the control box in one position.

The principles of the present invention are particularly useful in an x-ray examination table having a table top 1 which is mounted in a cantilevered fashion on a height-adjustable pedestal 2. The pedestal 2 is composed of telescoping parts 3, which are composed of box-shaped discrete parts which are telescoped into one another, and of an upper part 4, which rests on an upper telescopic part 3 and on which the table top 1 is detachably connected. A control box 5, which has a desk shape with an inclined top surface on which the control elements are positioned is arranged on the upper part 4. The control box 5 is mounted on the upper part 4 by means allowing longitudinal displacement so that the control box is dislocatable in the longitudinal direction of the table towards the free end of the table top 1. Accordingly, the control box 5 will have two working positions, with one working position illustrated in FIG. 1 and the second illustrated in FIG. 2.

Figure 2:
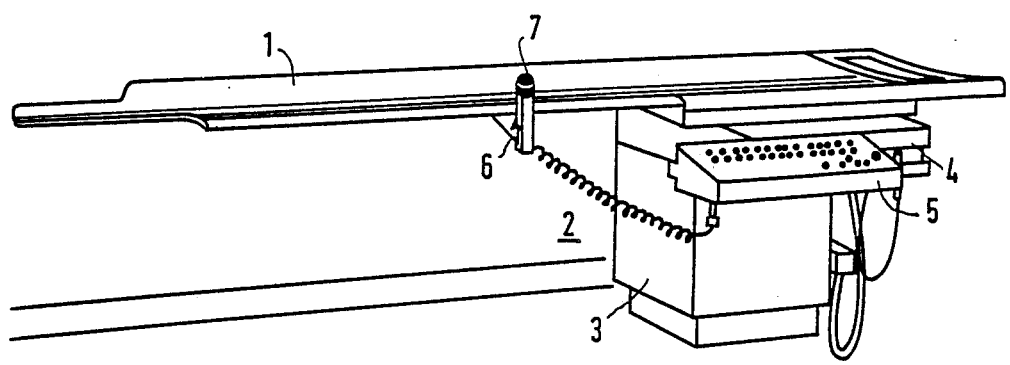
FIG. 2 is a perspective view of the x-ray examination table of the present invention with the control box being displaced to the other position.

As shown in FIG. 1, the control box is in the normal or first position. When the physician is working at the head area of the patient which is at an end of the table 1 opposite the pedestal 2, then the distance to the control box 5 in this normal position is relatively great. In order to facilitate easier reaching of the control box 5 for the physician, he can displace or slide the control box on the means for mounting towards the head end of the table into a second position shown in FIG. 2 flexible lines connect the box 5 to the pedestal 2 (as illustrated) and enable this dislocation. As illustrated, the means allowing longitudinal displacement includes the upper part having a side with a groove extending in said longitudinal direction and the control box has a projection on a back surface being received in the groove for sliding movement between the first and second positions.

The table top 1 further includes a holder 6 for a control element 7, which can be connected to the control box 5 of FIG. 1. A definite function is controllable by the control element 7 in a simple manner.

Although various minor modifications may be suggested by those versed in the art, it should be understood that we wish to employ within the scope of the patent granted hereon, all such modifications as reasonably and properly come within the scope of our contribution to the art.

We claim:

1. In an x-ray examination table having a table top with one end of the table top mounted on a pedestal which has a control box having an inclined upper surface, said box containing a plurality of control elements for the examination procedure being disposed on said upper surface, and an additional control element being connected to the control box via a control cable, the improvements comprising said pedestal having means for mounting the control box for displaceable movement on said pedestal in a longitudinal direction of the table top between two longitudinally spaced work positions, and a holder for the additional control element being mounted on the table top at a position spaced from the pedestal said means for mounting including groove in a side of the pedestal extending in said longitudinal direction and a projection on said control box slidably received in said groove to allow movement between said work positions.

* * * * *